(12) United States Patent
Chudik

(10) Patent No.: US 9,387,011 B2
(45) Date of Patent: Jul. 12, 2016

(54) ACROMIOCLAVICULAR JOINT REPAIR SYSTEM

(76) Inventor: Steven C. Chudik, Western Springs, IL (US)

(*) Notice: Subject to any disclaimer, the term of this patent is extended or adjusted under 35 U.S.C. 154(b) by 2900 days.

(21) Appl. No.: 11/701,845

(22) Filed: Feb. 2, 2007

(65) Prior Publication Data

US 2007/0270804 A1 Nov. 22, 2007

Related U.S. Application Data

(60) Provisional application No. 60/764,027, filed on Feb. 2, 2006.

(51) Int. Cl.
  A61B 17/56 (2006.01)
  A61B 17/68 (2006.01)
  A61B 17/06 (2006.01)
  A61B 17/16 (2006.01)
  A61B 17/86 (2006.01)
  A61B 17/88 (2006.01)
  B25B 15/00 (2006.01)
  A61B 17/17 (2006.01)
  A61B 17/04 (2006.01)
  A61F 2/08 (2006.01)

(52) U.S. Cl.
  CPC ......... *A61B 17/683* (2013.01); *A61B 17/06166* (2013.01); *A61B 17/1684* (2013.01); *A61B 17/8685* (2013.01); *A61B 17/8875* (2013.01); *A61F 2/0811* (2013.01); *B25B 15/001* (2013.01); *A61B 17/1714* (2013.01); *A61B 17/8897* (2013.01); *A61B 2017/0403* (2013.01); *A61B 2017/044* (2013.01); *A61B 2017/1775* (2013.01); *A61B 2017/1778* (2013.01); *A61F 2/0805* (2013.01); *A61F 2002/0829* (2013.01); *A61F 2002/0858* (2013.01); *A61F 2002/0888* (2013.01)

(58) Field of Classification Search
  CPC ....................................................... A61B 17/56
  USPC ......... 606/300, 301, 304–306, 309, 310, 319, 606/86 R
  See application file for complete search history.

(56) References Cited

U.S. PATENT DOCUMENTS

| | | | | | |
|---|---|---|---|---|---|
| 4,959,064 | A | * | 9/1990 | Engelhardt | 606/65 |
| 5,061,137 | A | * | 10/1991 | Gourd | 411/510 |
| 5,152,790 | A | * | 10/1992 | Rosenberg et al. | 623/13.14 |
| 5,409,490 | A | * | 4/1995 | Ethridge | 606/80 |
| 6,908,275 | B2 | * | 6/2005 | Nelson et al. | 411/487 |
| 7,488,323 | B2 | * | 2/2009 | Bacastow et al. | 606/86 R |
| 7,625,395 | B2 | * | 12/2009 | Muckter | 606/300 |
| 2002/0198527 | A1 | * | 12/2002 | Muckter | 606/73 |
| 2005/0192631 | A1 | * | 9/2005 | Grafton | 606/228 |

* cited by examiner

*Primary Examiner* — Christopher Beccia
(74) *Attorney, Agent, or Firm* — Gregory B. Beggs

(57) ABSTRACT

A system is disclosed for repairing and reconstructing a joint which has been injured by trauma, and especially an acromioclavicular joint. Means are disclosed to strengthen the repair or reconstruction and to maintain alignment while the ligaments in the joint heal, thus allowing more aggressive rehabilitation. A new joint repair tool is disclosed which is inserted into two separated bones adjacent to their respective articular joint surfaces to connect the two bones and approximate the adjacent bearing articular joint surfaces while still allowing motion between the two bones. Instruments to perform the methods are also disclosed.

11 Claims, 21 Drawing Sheets

ACROMIOCLAVICULAR JOINT REPAIR SYSTEM

This is a nonprovisional application which claims the filing date of the same applicant's provisional application Ser. No. 60/764,027 filed in the United States Patent and Trademark Office on Feb. 2, 2006.

This invention relates to systems for repairing and reconstructing injured acromioclavicular (hereafter "AC") joints. More particularly it relates to a novel joint repair tool and a related family of methods of orthopaedic surgery and instruments for repairing and reconstructing an injured acromioclavicular joint.

Except for the provisional application just referred to, there are no patent applications related to this one. Neither this application nor the provisional application upon which it relies is subject to any federally sponsored research or development or to any joint research agreement.

BACKGROUND OF THE INVENTION

Orthopaedic surgeons perform reparative or reconstructive surgery on joints which have been separated or dislocated by trauma. The goal of surgery is to properly align the adjacent bones of a joint and either repair or reconstruct the ligaments of the joint to maintain their position. With regard to the AC joint of the human shoulder (FIG. 1), the clavicle and acromion of the scapula (two bones of the AC joint) can be separated by traumatic injury. With significant separation, two sets of ligaments are damaged, particularly the AC and coracoclavicular (CC) ligaments. After reparative or reconstructive surgery to realign the AC joint, it is difficult to oppose the distracting forces at the joint while the AC and CC ligaments, or reconstructed ligaments, heal. Often during the early postoperative period, because the repair or reconstruction is not sufficiently strong, the AC joint may lose its alignment and re-separate. Methods, instruments and an implant to assist and strengthen the repair or reconstruction may maintain the alignment of the AC joint better while the repaired or reconstructed ligaments heal, allow an earlier more aggressive rehabilitation and quicker return to activities, and improve the outcome after AC joint surgery.

BRIEF SUMMARY OF THE INVENTION

The present invention discloses a new joint repair tool, and the methods and instruments associated with its use, in repairing and reconstructing injured and separated joints, including the AC joint.

Accordingly, one object of this invention is to provide a means to strengthen the repair or reconstruction, to better maintain the alignment of the AC joint while the repaired or reconstructed ligaments heal, to allow an earlier more aggressive rehabilitation and quicker return to activities, and to improve the outcome after AC joint surgery.

Another object of this invention is to provide a simple joint repair system to restore the proper alignment of two or more bones in a fashion that properly approximates the adjacent bearing articular joint surfaces while still allowing normal motion between the bones.

Another object of this invention is to provide a new joint repair tool which is inserted into two separate bones adjacent to their respective bearing articular joint surfaces to connect the two bones in a fashion that properly approximates the adjacent bearing articular joint surfaces but still allows motion between the two bones.

Another object of this invention is to provide a method and instruments to insert a new joint repair tool.

Another object of this invention is to provide a drill sleeve to protect the skin and soft-tissue, to direct a drill bit and create a passageway in a first superficial bone, to direct a pin guide, and to direct a second drill bit.

Another object of this invention is to provide a drill bit used to create a passageway in a first superficial bone.

Another object of this invention is to provide a calibrated pin guide to protect the skin and soft-tissue, to direct a guide pin through or by the first superficial bone into a deep second, and to measure the distance of the path to the second deep bone from the first bone.

Another object of this invention is to provide a guide wire to be placed into a second deep bone and to guide a cannulated drill bit into the second deep bone.

Another object of this invention is to provide a cannulated drill bit to create a hole in a second deep bone.

Another object of this invention is to provide a driver to insert a new joint repair tool into both the first and second bones.

Another object of this invention is to provide a method to repair or reconstruct the AC and/or the CC ligaments after inserting a new joint repair tool.

Another object of this invention is to provide a joint repair tool that may be used to treat other joints, including the ankle.

DETAILED DESCRIPTION OF THE INVENTION

Figure 1:
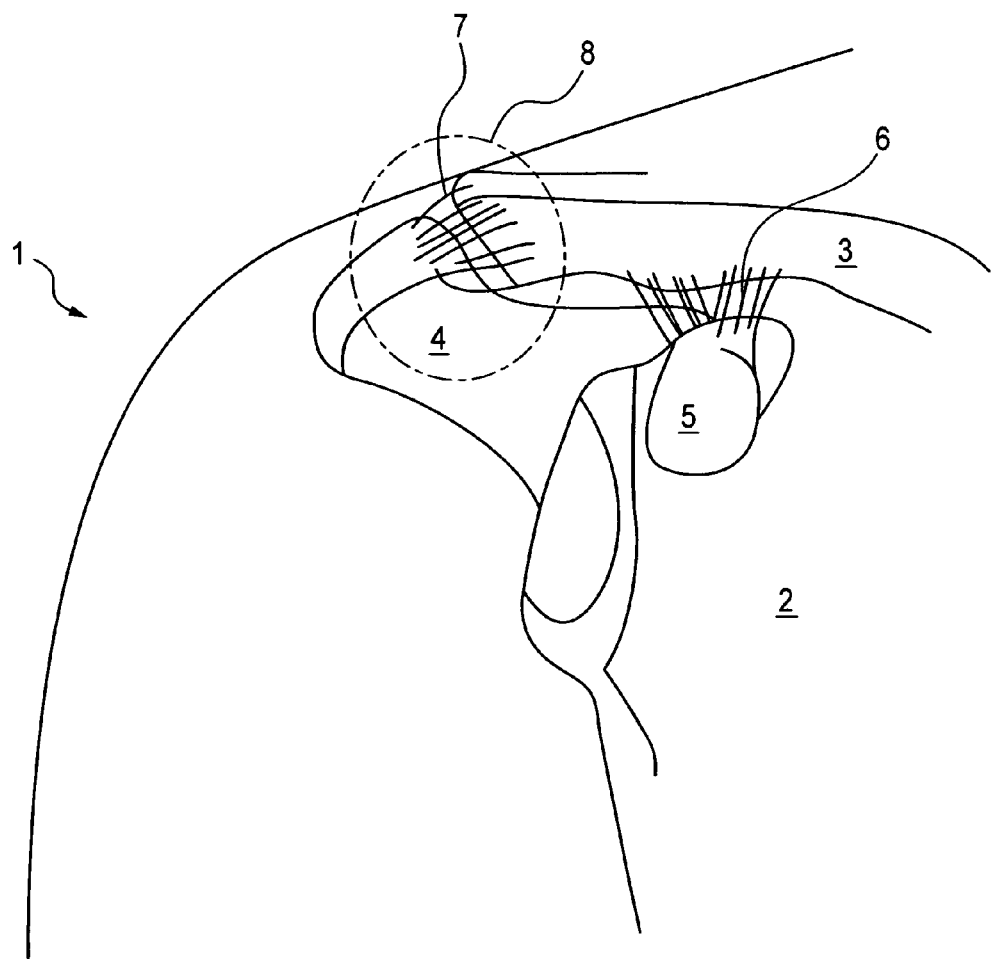
FIG. 1 is a perspective view of a shoulder with an uninjured acromioclavicular (AC) joint, acromioclavicular (AC) ligaments, and coracoclavicular (CC) ligaments.
Figure 2:
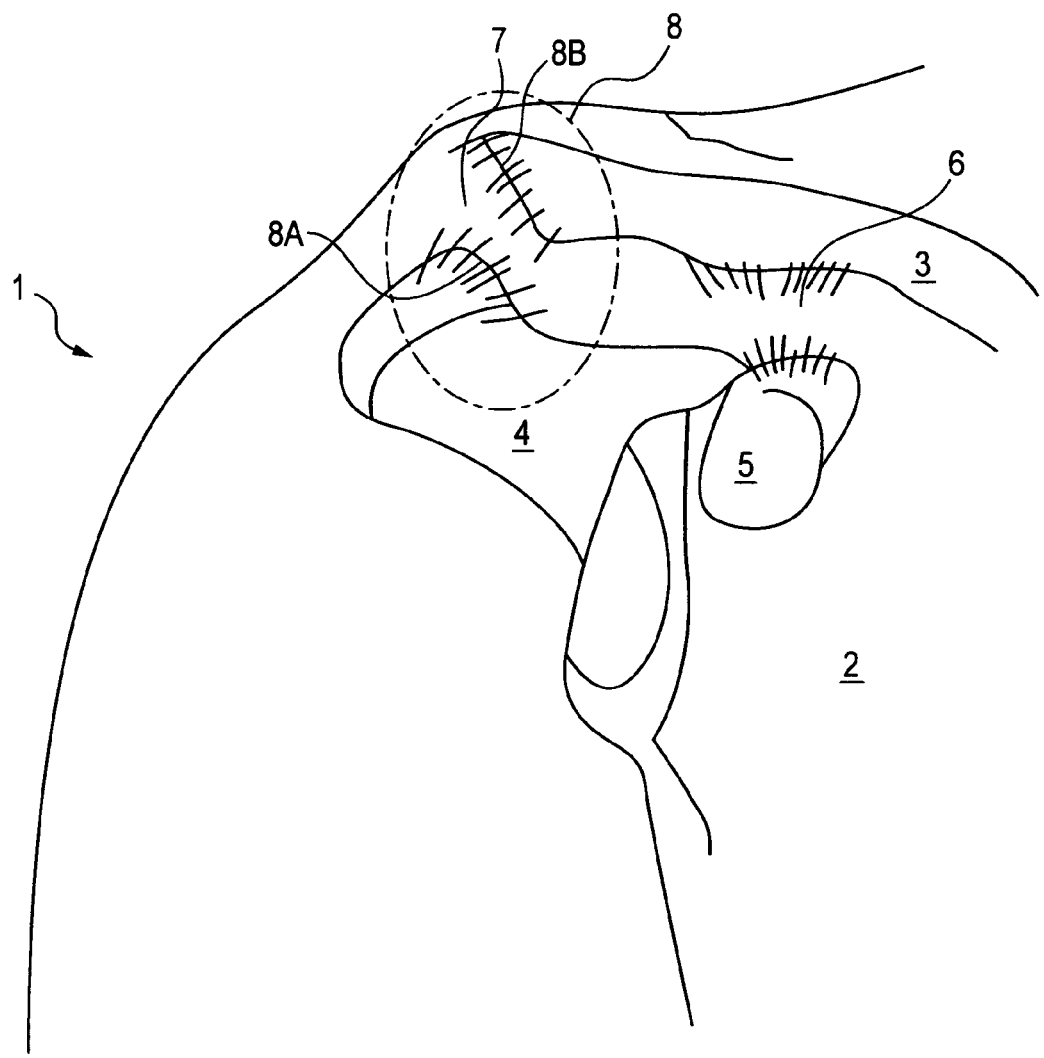
FIG. 2 is a perspective view of the shoulder in FIG. 1 showing a separation of the AC joint, illustrating a separation of the bearing articular joint surfaces of the clavicle and the acromion process of the scapula and disruption of both the acromioclavicular (AC) and coracoclavicular (CC) ligaments.
Figure 3:
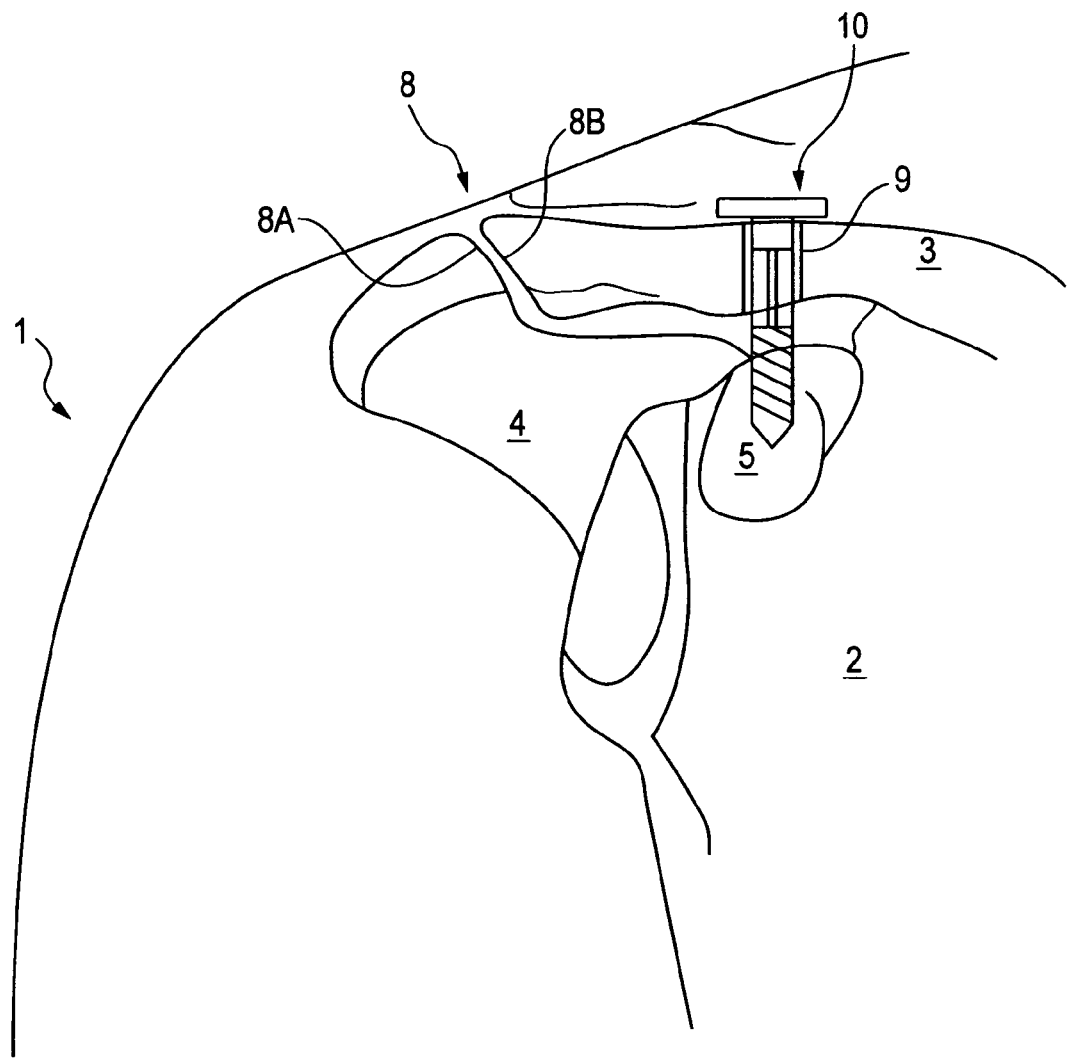
FIG. 3 is a perspective view of the novel joint repair tool of the present invention applied to the clavicle and coracoid process of the scapula in FIG. 2 to restore the proper relationship between the adjacent bearing articular joint surfaces of the clavicle and the acromion process of the scapula of the AC joint in accordance with the present invention.

The present invention relates to the use of a novel joint repair tool and to methods and associated instruments for performing joint reparative and reconstructive surgery, including, particularly, the acromioclavicular joint 8 of a shoulder 1 (see FIGS. 1, 2 and 3). The present invention includes novel techniques, a novel joint repair tool 10, a driver 25 for the joint repair tool 10, a drill sleeve 30, a first drill bit 34, a pin guide 40, a guide pin 43, a second drill bit 45 and a slotted graft passing pin 65.

Following a traumatic injury to the shoulder, the bearing articular surfaces 8A and 8B of the AC joint. 8 may be separated or dislocated by the disruption of the stabilizing acromioclavicular (AC) ligament 7 and the coracoclavicular (CC) ligament 6 (see FIGS. 1 and 2). Depending upon the severity of the separation or dislocation, the clavicle bone 3 can become separated from the acromion process 4 of the scapula bone 2 of shoulder 1. Surgery to repair or reconstruct the AC ligament 7 and CC ligament 6 may be required to realign clavicle bone 3 relative to the acromion process 4 of the scapula bone 2 and stabilize the bearing articular surfaces 8A and 8B of the AC joint 8. AC joint repair or reconstructive surgery can be performed utilizing the joint repair tool 10, FIGS. 3 and 8, to improve the fixation strength and allow better healing of the native or reconstructed ligaments.

Figure 4:
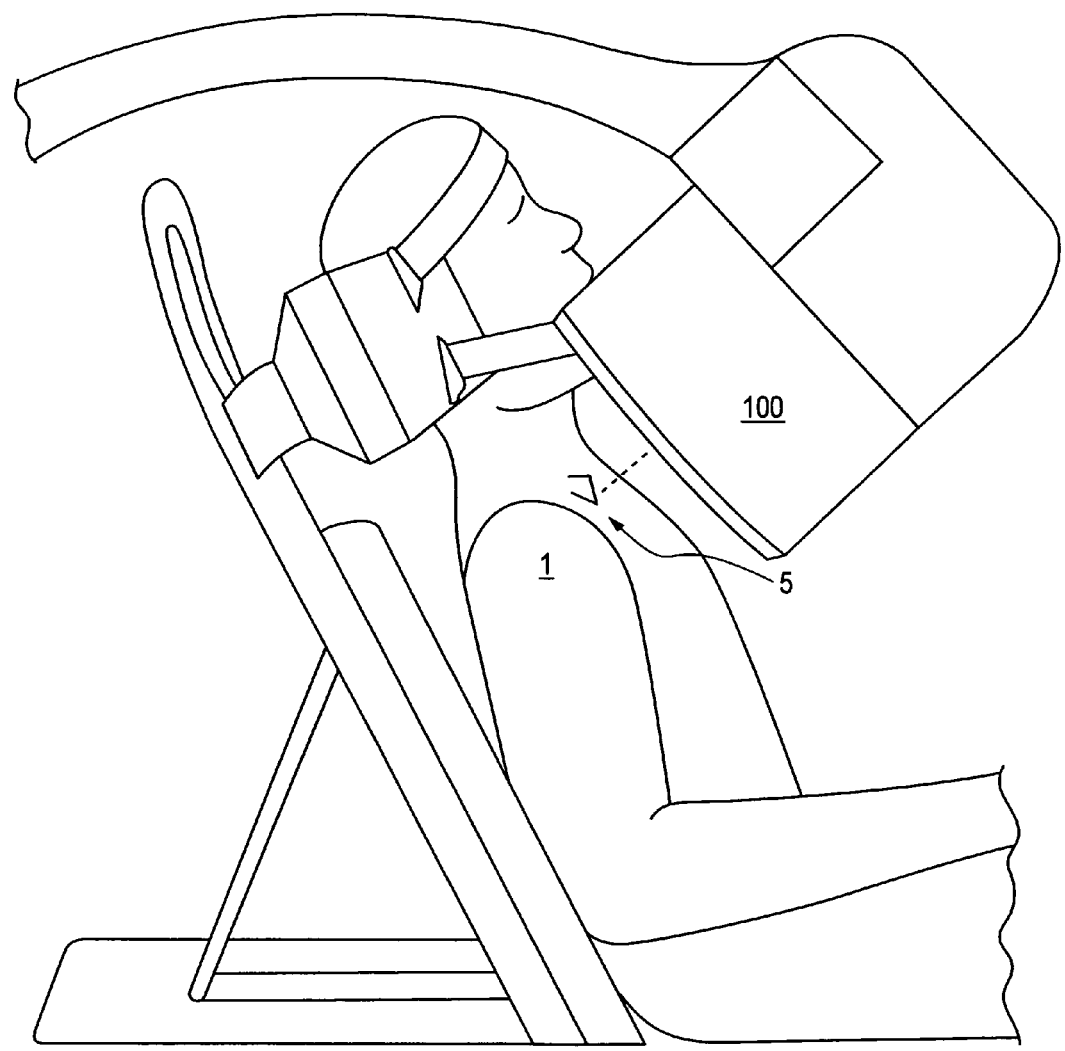
FIG. 4 is a schematic view of the manner of positioning a patient with a fluoroscopy C-arm unit, or similar intraoperative radiographic device, for performing the surgical technique of the present invention.

AC joint reparative and reconstructive surgery can be performed with the patient in a semi-upright beachchair position with the intraoperative fluoroscopy 100 centered over the coracoid 5 of shoulder 1, as shown in FIG. 4. Using the fluoroscopy 100, the surgeon identifies clavicle bone 3, acromion process 4 of scapula bone 2, coracoid process 5 of scapula bone 2 and the separated bearing surfaces 8A and 8B of AC joint 8. He creates a limited exposure through the skin and soft-tissue over the superficial aspect of the superficial bone, clavicle 3, in line with the deep bone, the base of coracoid process 5 of scapula 2.

Figure 5:
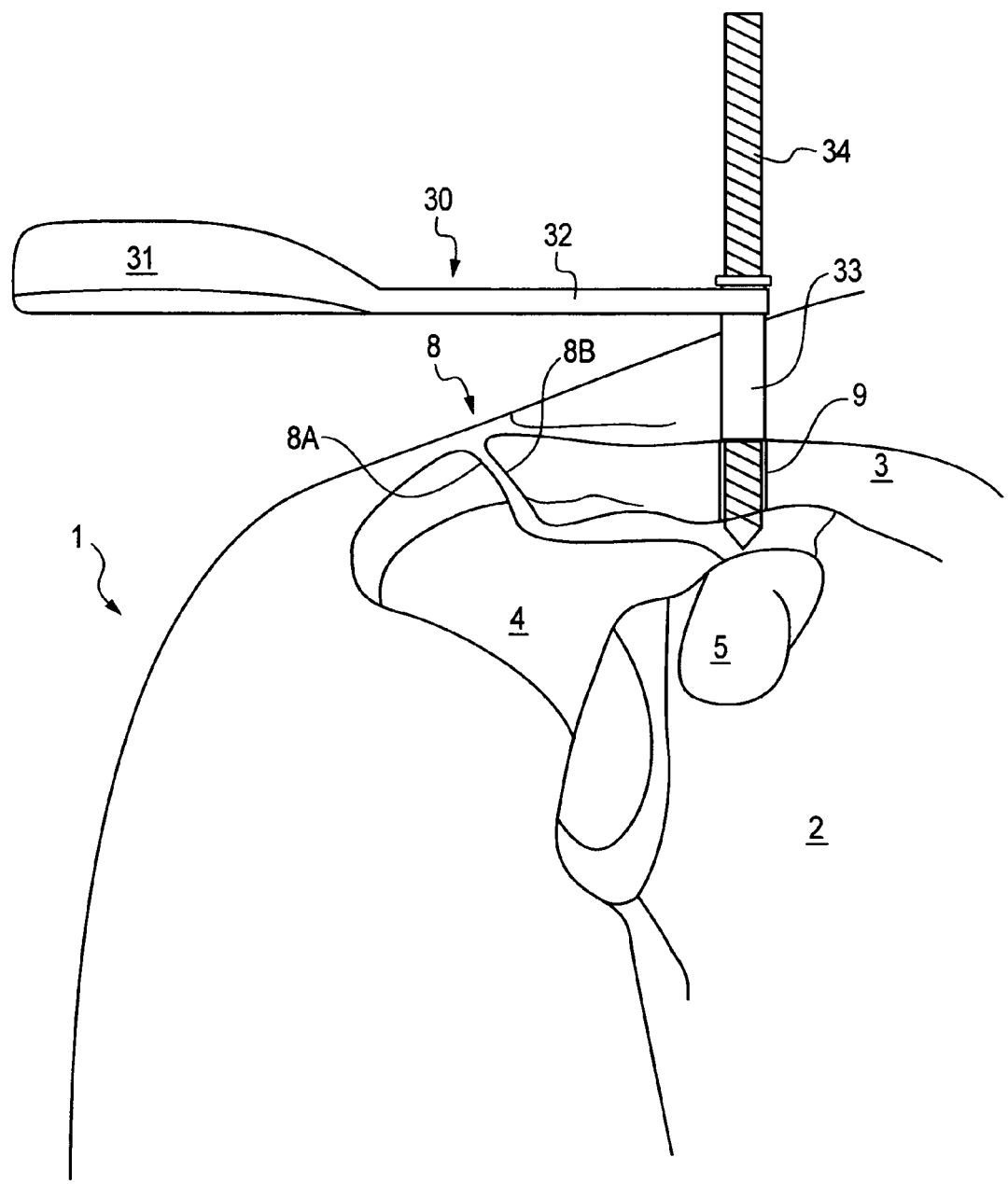
FIG. 5 is a schematic view of the manner of drilling a passageway in a first bone, the clavicle, in line with a second bone, the coracoid process of the scapula, in accordance with the present invention.

After exposing the superficial surface of the superficial bone, clavicle 3, the surgeon uses drill sleeve 30 with first drill bit 34 to create passageway 9 through clavicle 3 as shown in FIG. 5. Drill sleeve 30 includes a handle 31, a shaft 32 and a protective guide tip 33. The protective guide tip 33 is a thin but rigid tube which directs first drill bit 34 while protecting the surrounding soft-tissue. The inner diameter of protective tip 33 corresponds to the outer diameter of first drill bit 34 such that the direction of first drill bit 34 is well-controlled by tip 33 and runs smoothly within it. The outer diameter of first drill bit 34 ranges up to 1.5 mm, and preferable is in the range of 4 mm to 6 mm.

The surgeon uses intraoperative fluoroscopy 100 to assist in forming passageway 9 with the first drill bit 34. Initially, protective guide tip 33 of drill sleeve 30 is centered over the superficial bone, clavicle 3, in line with the deep bone, the base of the coracoid process 5 of scapula 2. The first drill bit 34 is introduced into protective guide tip 33 and advanced through clavicle 3 aiming for the base of coracoid process 5 of scapula 2. Simultaneously, the surgeon views the creation of passageway 9 with live fluoroscopy 100.

Figure 6:
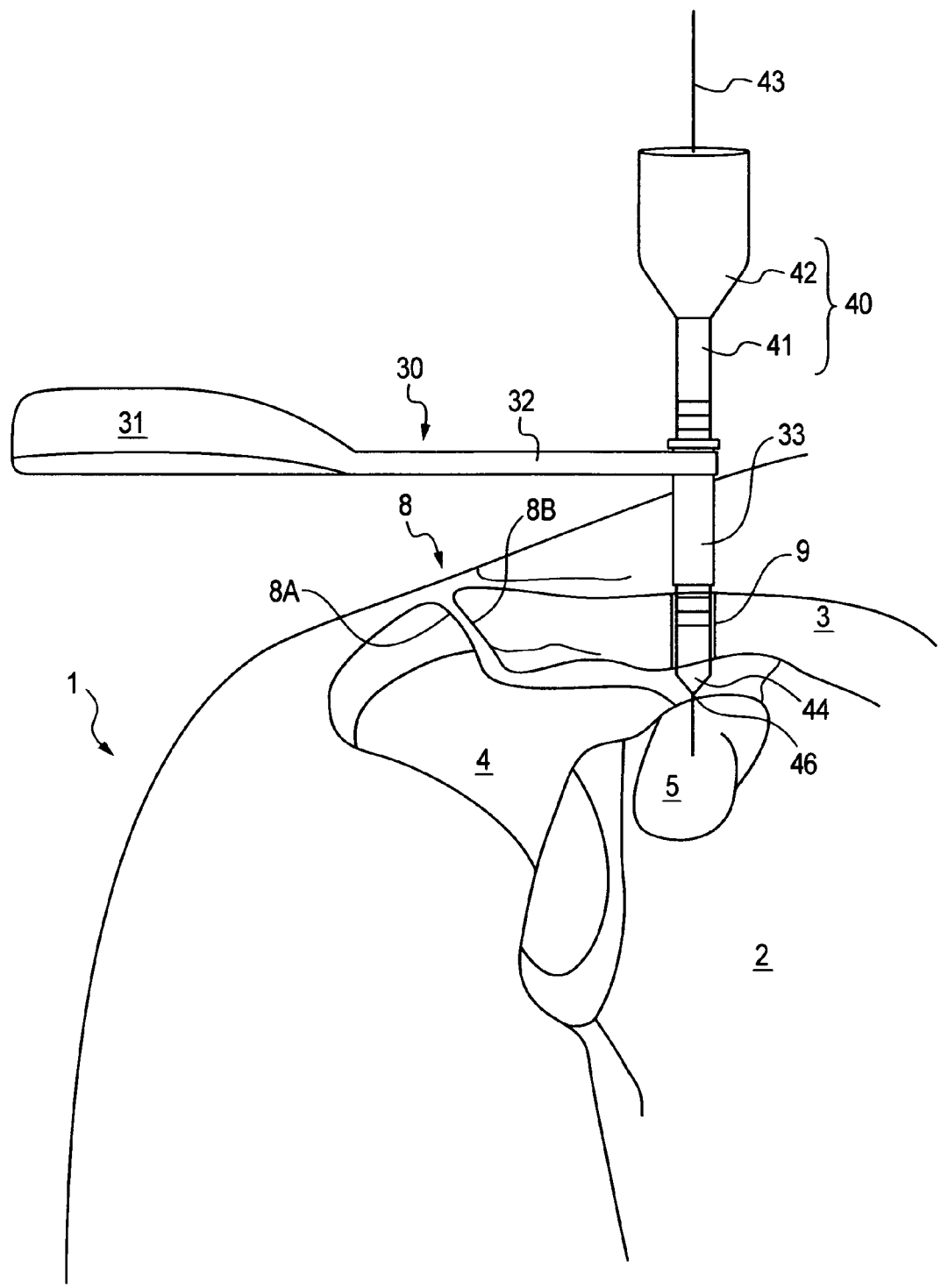
FIG. 6 is a schematic view of the shoulder of FIG. 5 showing the manner of inserting a guide pin through the passageway in the first bone, the clavicle, into the second bone, the coracoid process of the scapula, utilizing a drill sleeve and pin guide in accordance with the present invention.

Once passageway 9 is created through clavicle 3, the pin guide 40 is inserted into the clavicular passageway 9 upon the base of the coracoid process 5 of scapula 2 to assist in placing the guide pin 43 (see FIG. 6). Preferably, although not necessarily, the pin guide 40 may be inserted through protective guide tip 33 of drill sleeve 30.

The pin guide 40 possesses a blunt pointed tip 44, a long calibrated shaft 41, a handle 42 and a longitudinal cannulation 46. The blunt pointed tip 44 is designed to easily fit through the clavicular passageway 9 and to assist with proper placement of the guide pin 43, using palpitation and fluoroscopic guidance 100, upon the most superficial and central aspect of the bony crown of the base of the coracoid process 5 of scapula 2. The long calibrated shaft 41 has two sets of calibrations, one referenced from the top of protective guide tip 33 and the other from the superficial surface of the superficial bone, clavicle 3, in order to allow measurement of the length of the superficial bone clavicular passageway 9 and the remaining distance to the deep bone, the coracoid process 5 of scapula 2.

The outer diameter of shaft 41 of pin guide 40 is smaller than the outer diameter of first drill bit 34 and the inner diameter of clavicular passageway 9 in order to allow pin guide 40 sufficient freedom of movement within the passageway.

Figure 7:
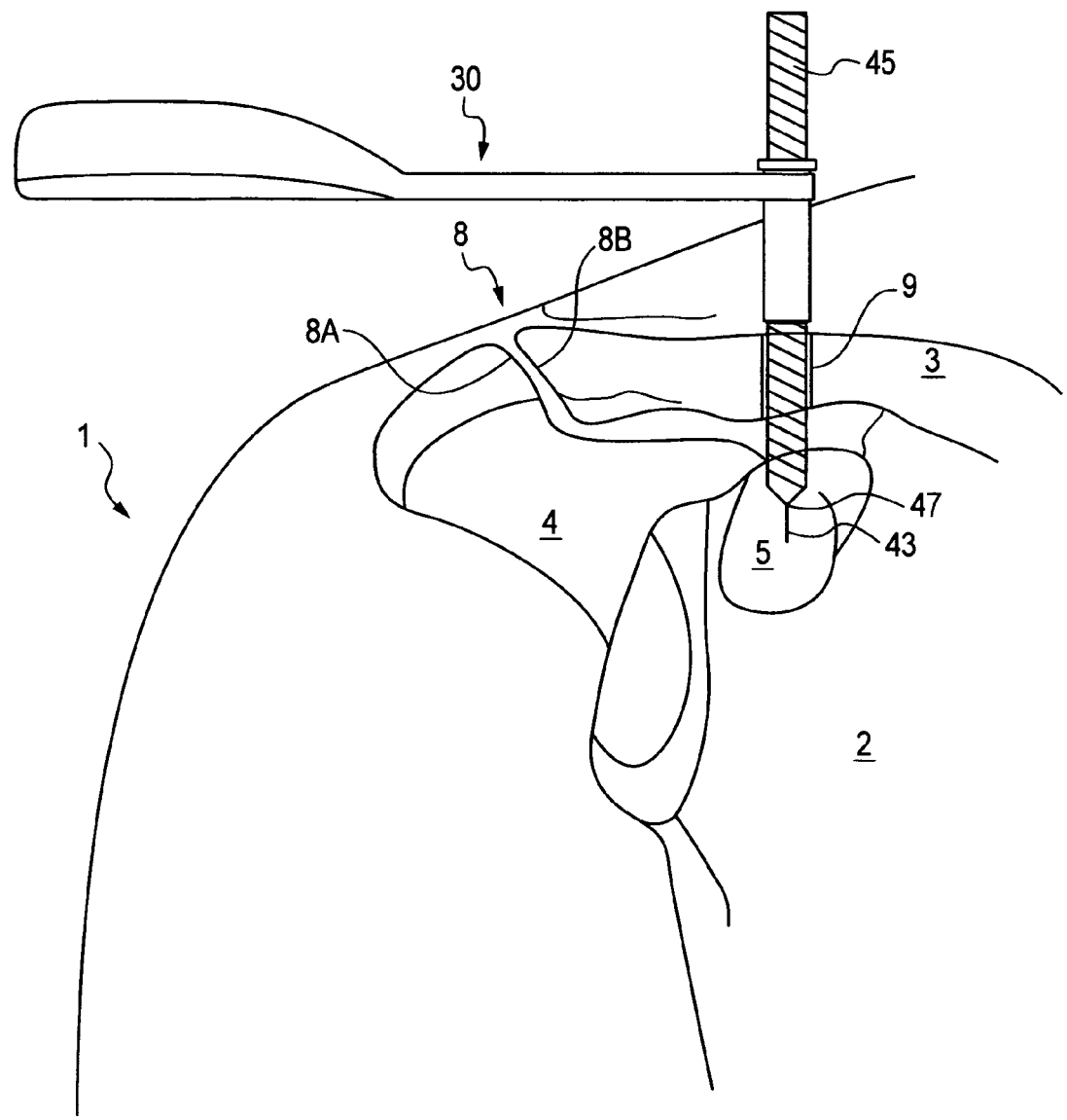
FIG. 7 is a schematic view of the shoulder of FIG. 6 showing the manner of drilling a hole in the second bone, the coracoid process of the scapula, through a passageway in the first bone, the clavicle, over the guide pin in accordance with the present invention.

With the pin guide 40 in proper position, guide pin 43 is drilled through central cannulation 46 of the pin guide 40 through the clavicular passageway 9 into the deep bone, the base of the coracoid process 5 of scapula 2, under live fluoroscopy 100. Then, with the guide pin 43 in proper position in the coracoid process 5 of scapula 2, second drill bit 45 is run over guide pin 43 through clavicular passageway 9 to drill a hole in the coracoid process 5 of scapula 2 (FIG. 7). Second drill bit 45 may be run through drill sleeve 30 in order to protect the surrounding soft-tissues. There is a central longitudinal cannulation 47 in second drill bit 45 to direct the bit over guide pin 43. The outer diameter of second drill bit 45 is smaller than the outer diameter of first drill bit 34 and of the inner diameter of clavicular passageway 9 in order to allow second drill bit 45 sufficient freedom of movement within clavicular passageway 9.

Figure 8:
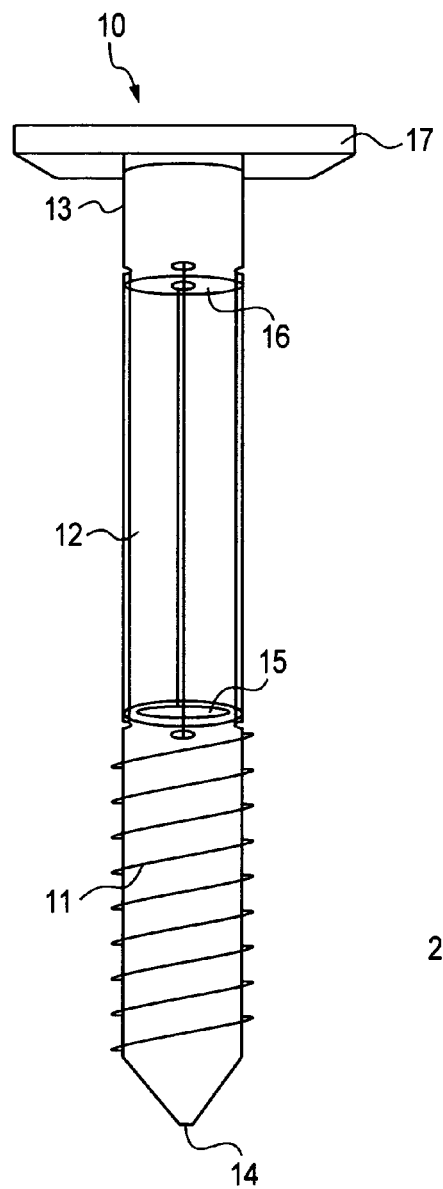
FIG. 8 is a further perspective view of the joint repair tool of FIG. 3.

Once the bones are exposed and prepared, the joint repair tool 10 may be inserted (FIG. 8). Tool 10 is inserted into the two separate bones, the clavicle 3 and the scapula 2, adjacent to their respective bearing articular joint surfaces 8A and 8B to connect the bones in a fashion which properly approximates the adjacent bearing articular joint surfaces 8A and 8B but still allows motion between the bones.

Figure 9A:
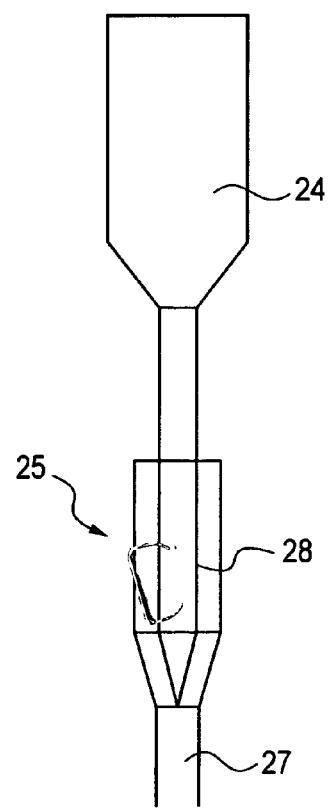
FIG. 9A is a perspective view of a portion of a driver instrument for use with the joint repair tool of FIGS. 3 and 8 in accordance with the present invention.
Figure 9:
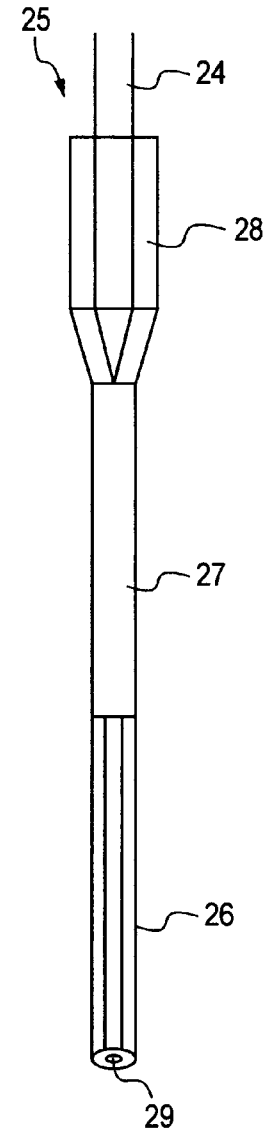
FIG. 9 is a perspective view of a portion of a driver instrument for use with the joint repair tool of FIGS. 3 and 8 in accordance with the present invention.
Figure 9B:
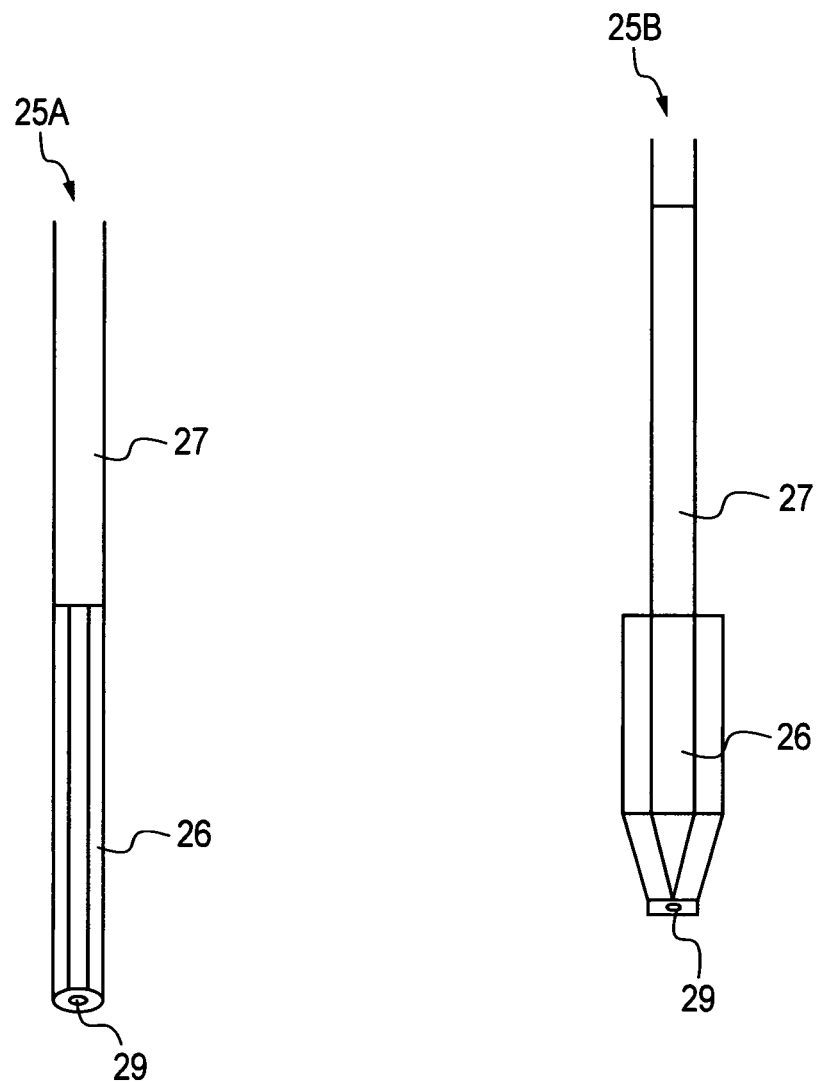
FIG. 9B is a perspective view of portions of a driver instruments for use with the joint repair tool of FIGS. 3 and 8 in accordance with the present invention.
Figure 10:
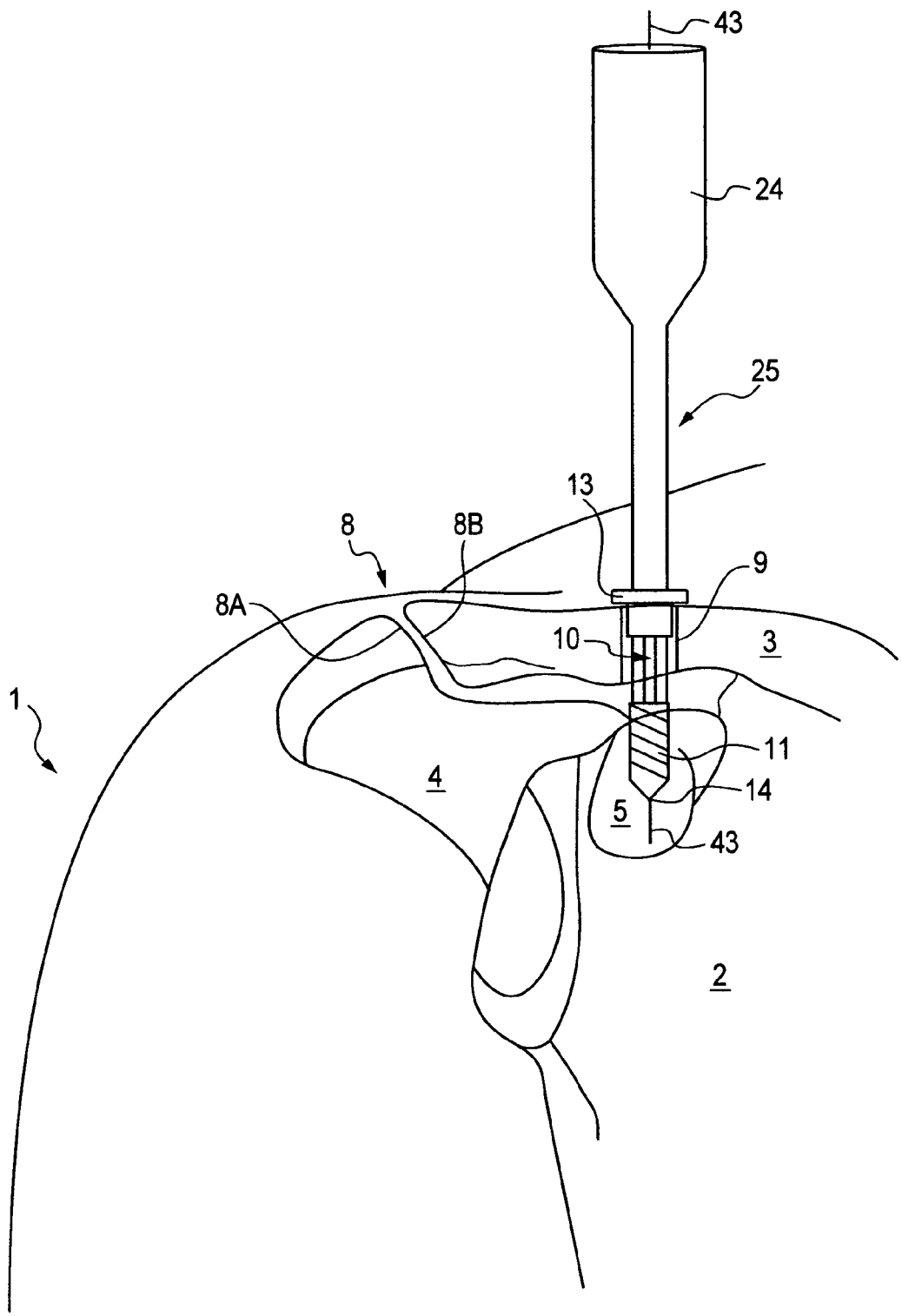
FIG. 10 is a schematic view of the manner of inserting the joint repair tool of FIGS. 3 and 8 through the passageway in the first bone, the clavicle, into the second bone, the coracoid process of the scapula, over the guide pin using the driver of FIG. 9 in accordance with the present invention.
Figure 11:
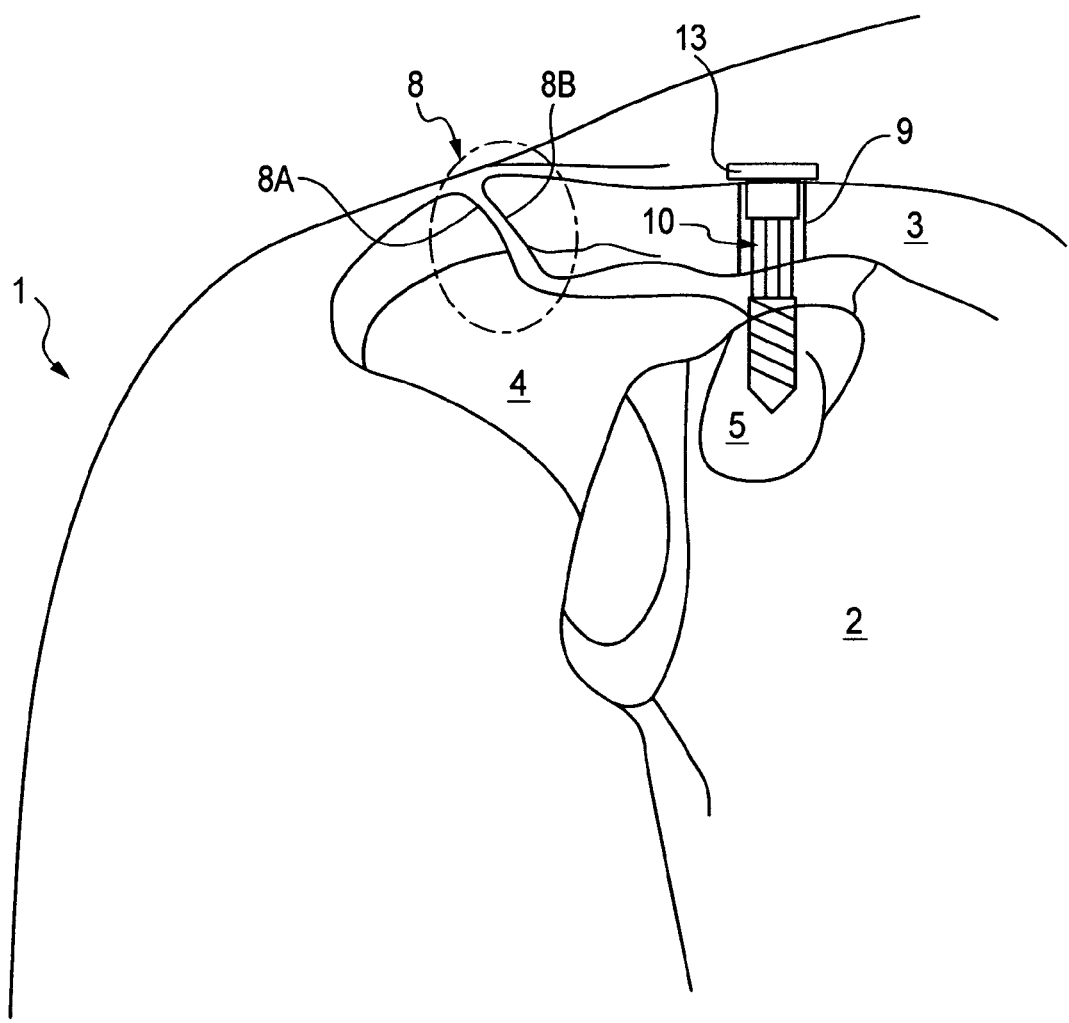
FIG. 11 is a perspective view of the joint repair tool of FIGS. 3 and 8 applied to the clavicle and coracoid process of the scapula to restore the proper relationship between the adjacent bearing articular joint surfaces of the clavicle and acromion process of the scapula of the AC joint in FIGS. 1 and 2 in accordance with the present invention.
Figure 12:
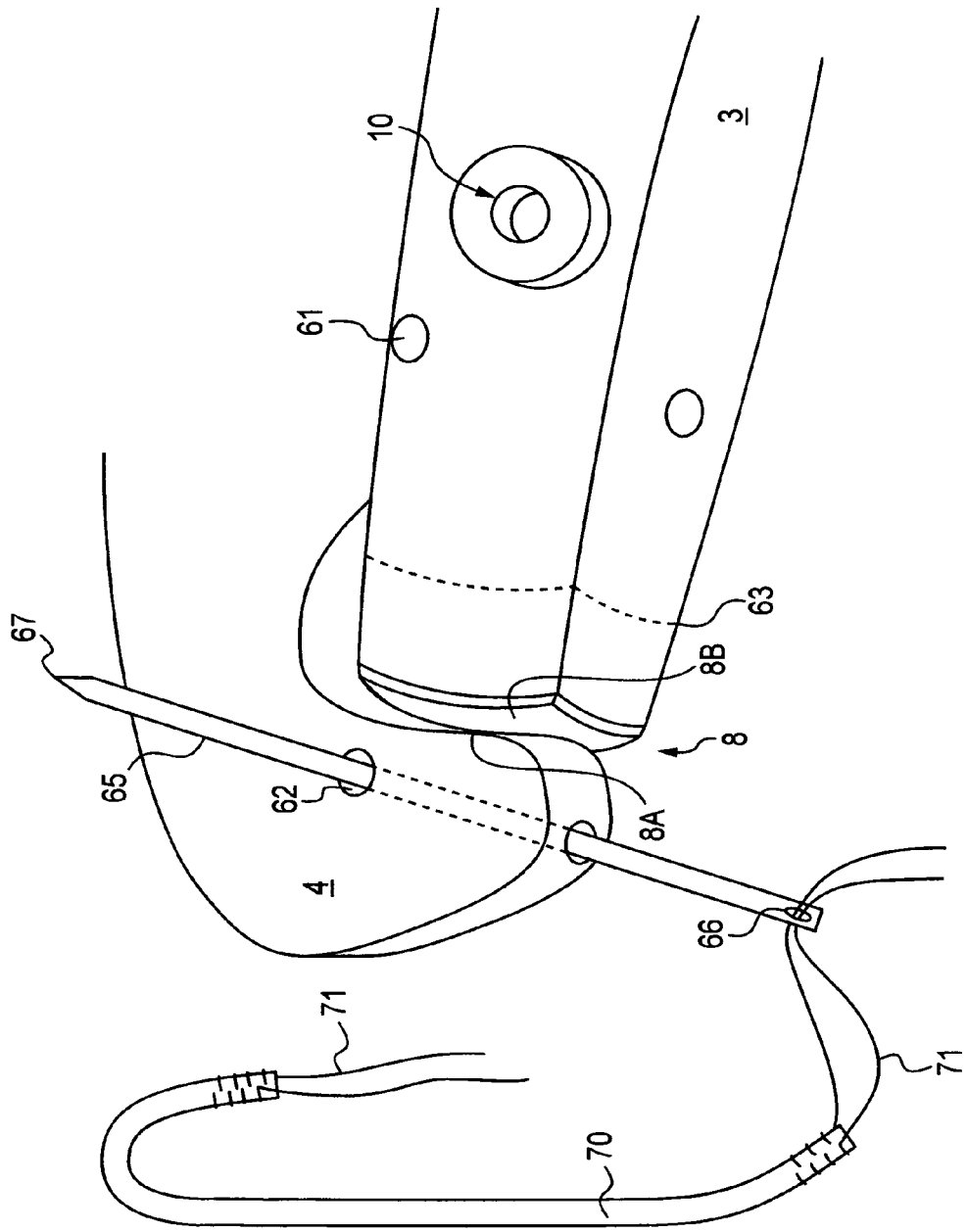
FIG. 12 is an enlarged view of an AC joint of a shoulder of FIGS. 1 and 2 illustrating Step 1 of the manner of reconstructing the AC joint ligaments using a free soft-tissue graft along with the joint repair tool of FIG. 3 in accordance with the present invention.
Figure 13:
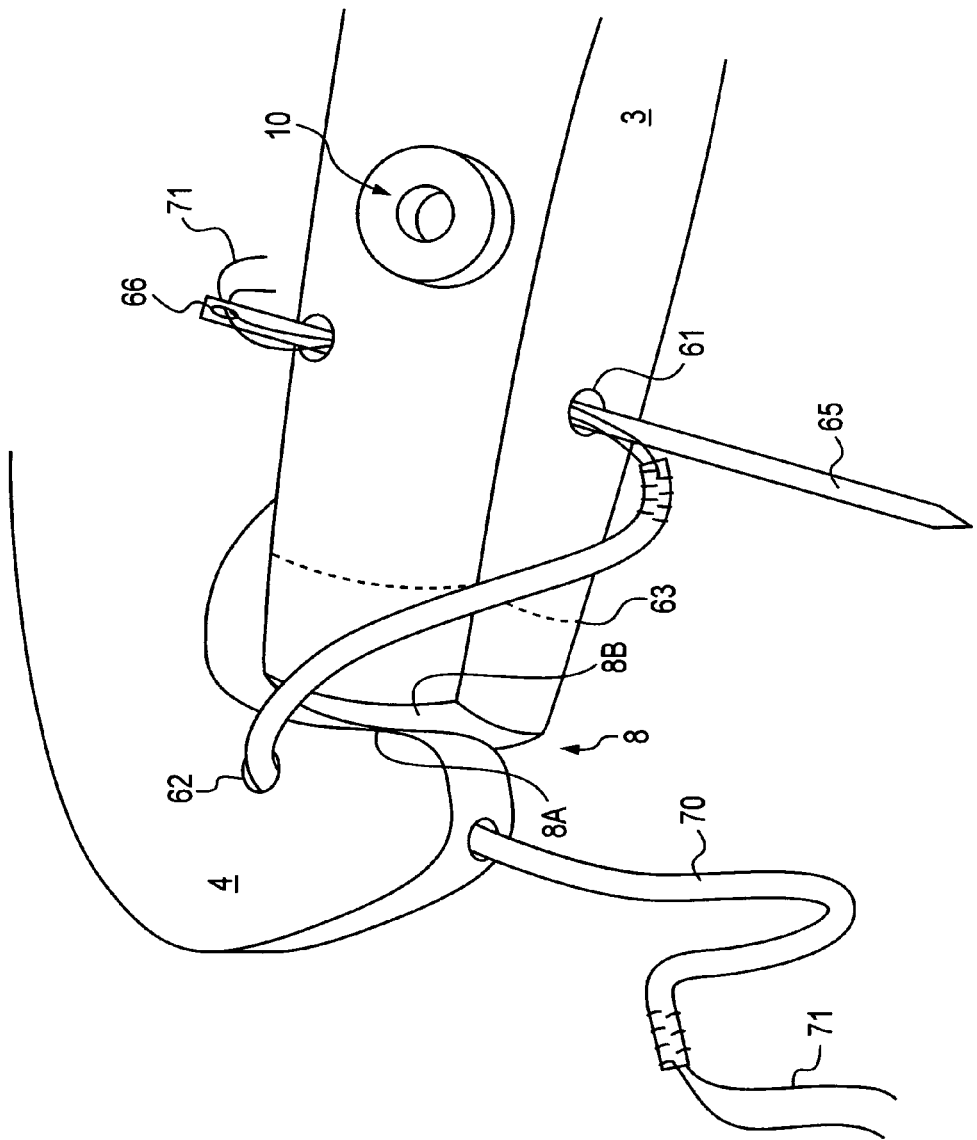
FIG. 13 is an enlarged view of the shoulder portion of FIG. 12 illustrating Step 2 of the manner of reconstructing the AC joint ligaments using the free soft-tissue graft along with the joint repair tool in accordance with the present invention.
Figure 14:
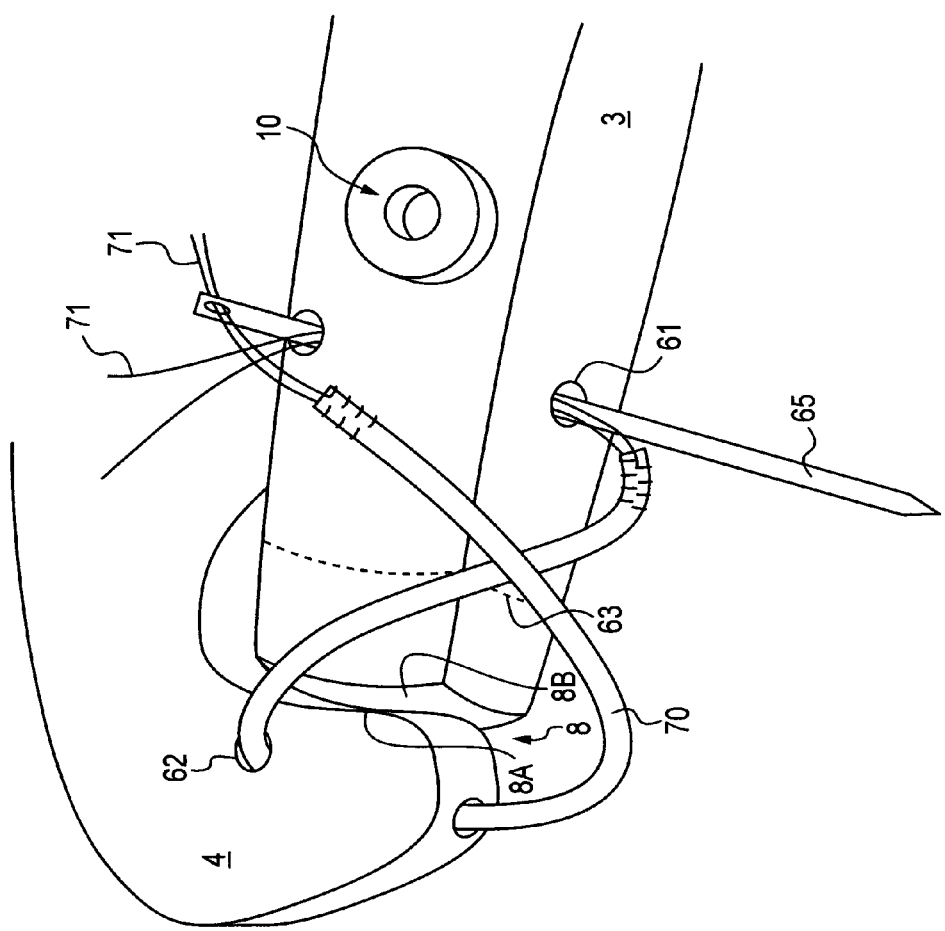
FIG. 14 is an enlarged view of the shoulder portion of FIG. 12 illustrating Step 3 of the manner of reconstructing the AC joint ligaments using the free soft-tissue graft along with the joint repair tool in accordance with the present invention.
Figure 15:
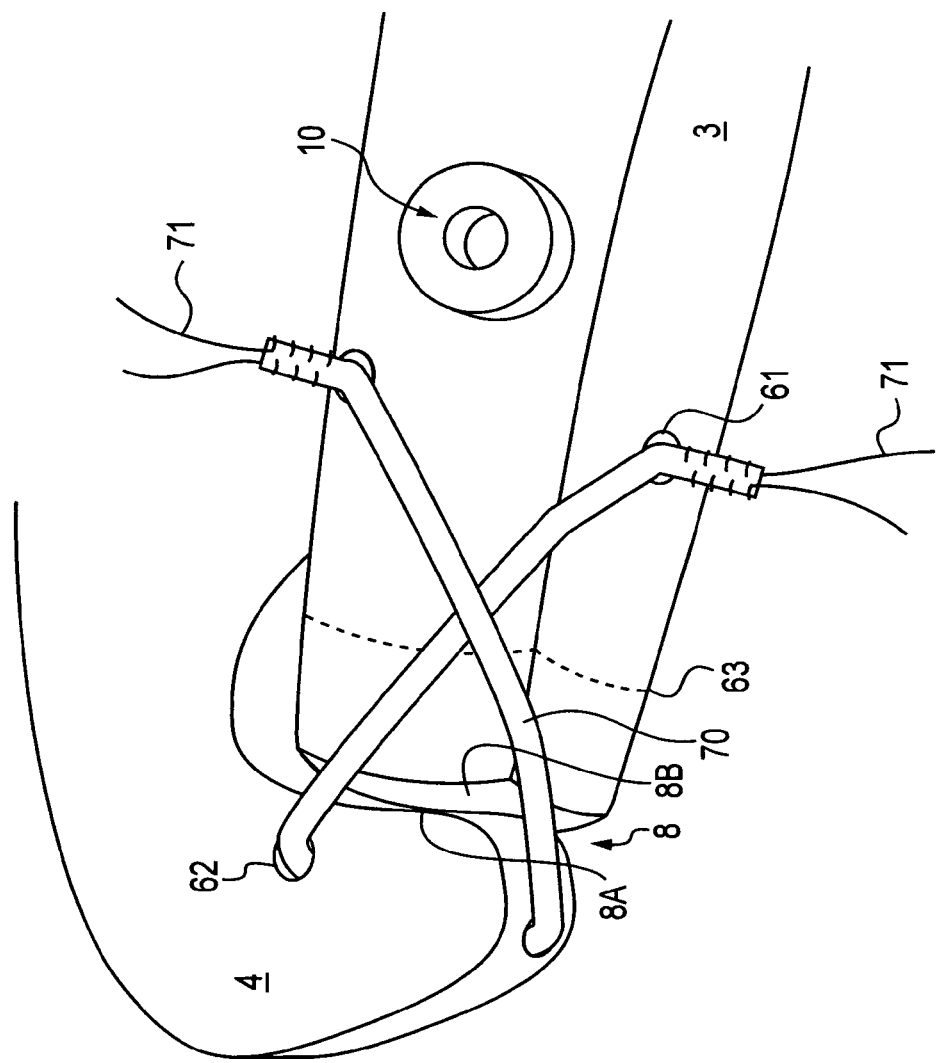
FIG. 15 is an enlarged view of the shoulder portion of FIG. 12 illustrating Step 4 of the manner of reconstructing the AC joint ligaments using the free soft-tissue graft along with the joint repair tool in accordance with the present invention.

The joint repair tool 10 is made of durable materials which are non-absorbable, bio-absorbable or capable of biointegration. Tool 10 possesses two bone attachment components, first bone attachment component 11 and second bone attachment component 13, and a mobile intermediate component 12. Components 11, 12 and 13 may be combined as a single fixed unit or made as separate components which may be disassembled and later assembled for use. The bone attachment components 11 and 13 possess geometry and surface properties which provide a purchase in or on the bones such as the coracoid process 5 of the scapula 2 and the clavicle 3. Also, there are driver connection sites on the bone attachment components 11 and 13 which interface with a single driver 25 or separate drivers 25A and 25B to assist with insertion (FIGS. 9, 9A, and 9B). In form, the bone attachment components may be of similar or dissimilar design, varying according to their anatomic location for application, and they may attach to the bones by similar or dissimilar mechanisms.

With the bone attachment components 11 and 13 connected to their respective bones, the mobile intermediate component 12 with its fixed or removable connections to the bone attachment components operatively engaged with those components 11 and 13 maintains clavicle 3 and scapula 2 and their adjacent bearing articular joint surfaces 8A and 8B in proper relationship while still allowing normal physiological motion of the bones and their joint surfaces.

In one example (see FIG. 8), the first bone attachment component 11 possesses threads and a leading tip which allows it to be drilled into scapula 2 or inserted into a hole in scapula 2. The second bone attachment component 13 possesses a "top hat shape" with the "brim" acting as a stop 17 of broader dimension than the crown of the hat to capture clavicle 3 and maintain the relationship of clavicle 3 to scapula 2 by means of the mobile intermediate component 12 being connected to the first bone attachment component 11 in scapula 2. In this example, mobile intermediate component 12 is a flexible wire or suture which allows the normal physiological motion between clavicle 3 and scapula 2 once the joint repair tool 10 is secured to those bones. The wire or suture of component 12 may be formed as a number of fixed loops or as loops with free ends which can be tensioned and secured after the first and second bone attachment components 11 and 13 are joined to scapula 2 and clavicle 3. The loops may vary in length up to 100 mm, but are preferably in the range of 5 mm to 25 mm. Bone attachment components 11 and 13 are formed with a cannulation 14 which allows them to be inserted in clavicle 3 and scapula 2 over the guide wire 43, if desired, although they may be inserted without using guide wire 43 if that is preferred.

In this example, a single driver 25 can be used to insert the joint repair tool 10, as shown in FIGS. 9, 9A, 9B, 10, and 11. Driver 25 includes a handle 24, a cannulation 29 for guide wire 43, a shaft 27, and two working segments, a first working 26 and a second working segment 28, each with specific cross-sectional geometry (a hexagon, or a star, for example), which interface with the driver connection sites 15 and 16, respectively, on the joint repair tool 10. The shaft 27 of the driver may be of a fixed or adjustable length which matches the length of the mobile intermediate component 12 of the joint repair tool 10. The joint repair tool 10 is loaded onto driver 25 by positioning the first working segment 26 through the second bone attachment component 13 and into the cannulation 14 of the first and second bone attachment components 11 and 13. This loading step engages the first working segment 26 of driver 25 with driver connection site 15 of the first bone attachment component 11 and the second working segment 28 of driver 25 with driver connection site 16 of the second bone attachment component 13. Because the driver 25 engages both bone attachment components 11 and 13 at the same time, the driver 25 can apply the joint repair tool 10 to and into both bones, the clavicle 3 and the scapula 2, simultaneously, thus maintaining a constant spatial and connective relationship between the two bone attachment components 11 and 13 of tool 10 without twisting mobile intermediate component 12.

In this example, the proper length of the joint repair tool 10 is based upon previous measurements made by calibrated pin guide 40. A properly sized joint repair tool 10 is inserted with the driver 25 through the superficial clavicular bone passageway 9 into the deep bone, coracoid process 5 of scapula 2, over guide wire 43. First bone attachment component 11 is advanced into the deep bone, coracoid process 5 of scapula 2, until the second bone component 13 of tool 10 engages the superficial bone with its stop 17 and restores a proper relationship between the adjacent bearing articular surfaces 8A and 8B of the acromion process 4 of scapula 2 and clavicle 3 (see FIGS. 10, 11). Guide wire 43, if used, and driver 25 are then removed.

Before or after inserting the joint repair tool 10, resection arthroplasty of the bearing articular surfaces 8A and 8B of the AC joint 8 may be performed using conventional open or arthroscopic techniques for irreparable damage to those bearing articular surfaces 8A and 8B.

With the joint repair tool 10 in position, primary repair of the acromioclavicular (AC) ligament 7, as well as of the coraclavicular (CC) ligament 6, can be performed (see FIG. 2). Primary repair can be performed using conventional suture or suture anchor techniques to sew the ligaments together, and that repair can be augmented by using a second joint repair tool 10, designed, as described above, for use in clavicle 3 and acromion process 4 of scapula 2 to help restore the proper relationship between adjacent bearing articular joint surfaces 8A and 8B.

Figure 16:
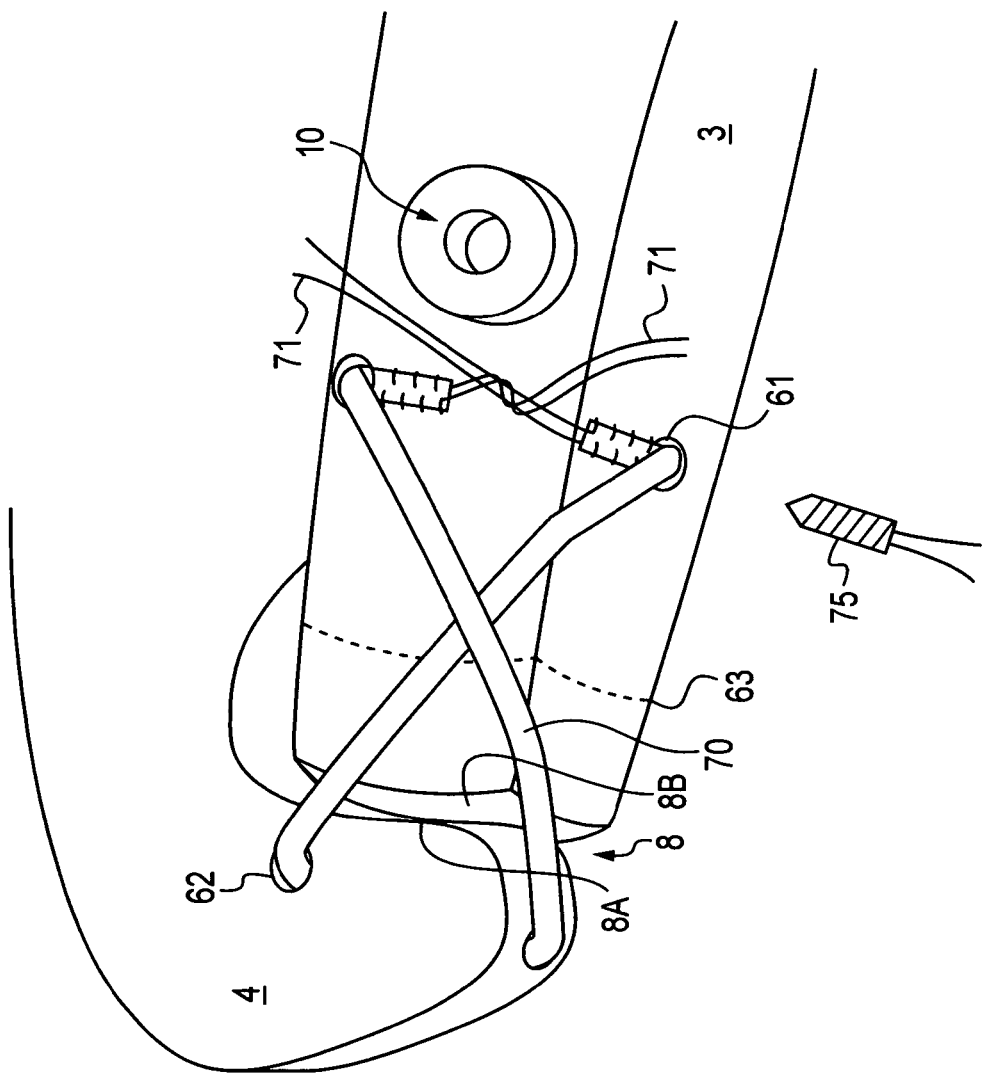
FIG. 16 is an enlarged view of the shoulder portion of FIG. 12 illustrating Step 5 of the manner of reconstructing the AC joint ligaments using the free soft-tissue graft along with the joint repair tool in accordance with the present invention.

Alternatively, reconstruction of the AC joint using free soft-tissue autografts or allografts 70 can be used, as shown in FIGS. 2, 12, 13, 14, 15, 16, 17 and 18. To reconstruct the acromioclavicular ligaments, tunnels 61 and 62 are constructed, respectively, in clavicle 3 and in the acromion process 4 of scapula 2. After the tunnels 61 and 62 are drilled, a passing pin 65 with a sharp leading tip 67 and a slot 66 is installed which assists with passing a free graft 70 having attached sutures 71 across the bearing articular surfaces 8A and 8B of the AC joint 8 (see FIGS. 12, 13, 14 and 15). With the free graft 70 in position at the AC joint, the ends with attached sutures 71 are tensioned and secured by tying or fastening the sutures, and/or, if preferred, inserting a conventional interference fixation device or screw in bone tunnel 61 along with the free ends of graft 70 as shown in FIG. 16.

Figure 17:
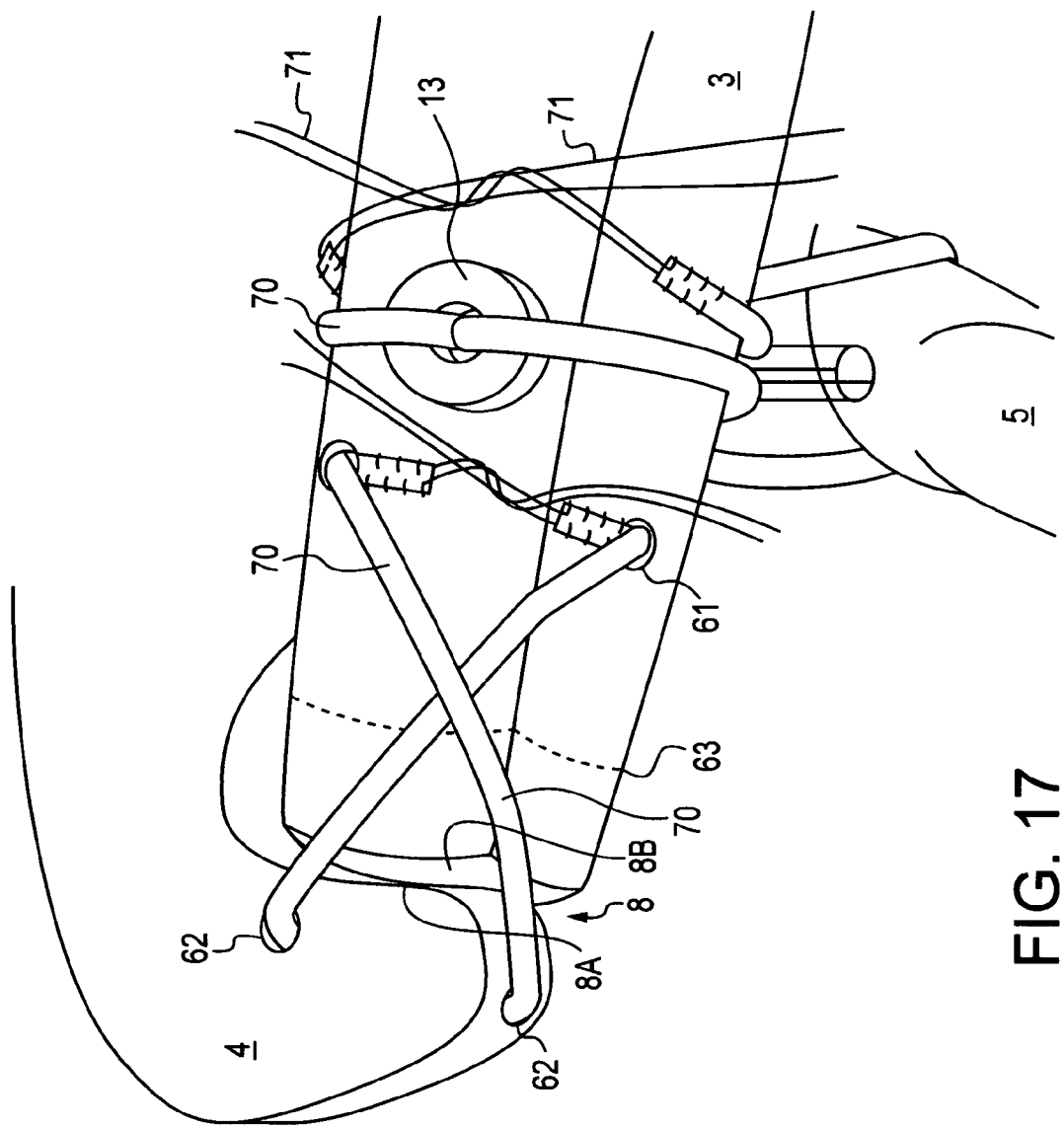
FIG. 17 is an enlarged view of the shoulder portion of FIG. 12 illustrating a manner of reconstructing the AC and CC joint ligaments using a free soft-tissue graft along with the joint repair tool of FIG. 3 in accordance with the present invention.
Figure 18:
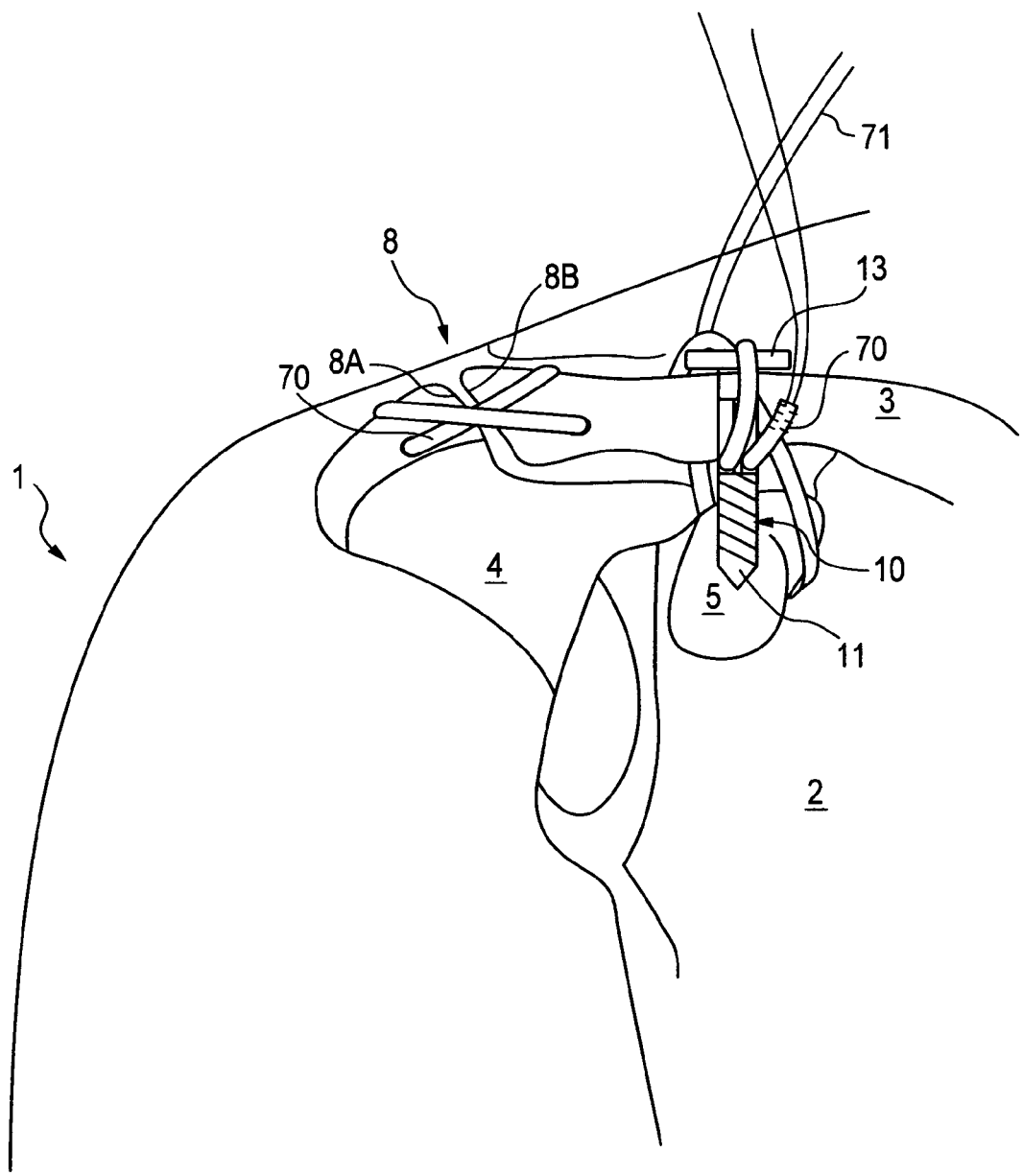
FIG. 18 is a schematic view of the shoulder of FIGS. 1 and 2 illustrating an alternate manner of reconstructing the AC and CC joint ligaments using a free soft-tissue graft along with the joint repair tool of FIG. 3 in accordance with the present invention.
Figure 19A:
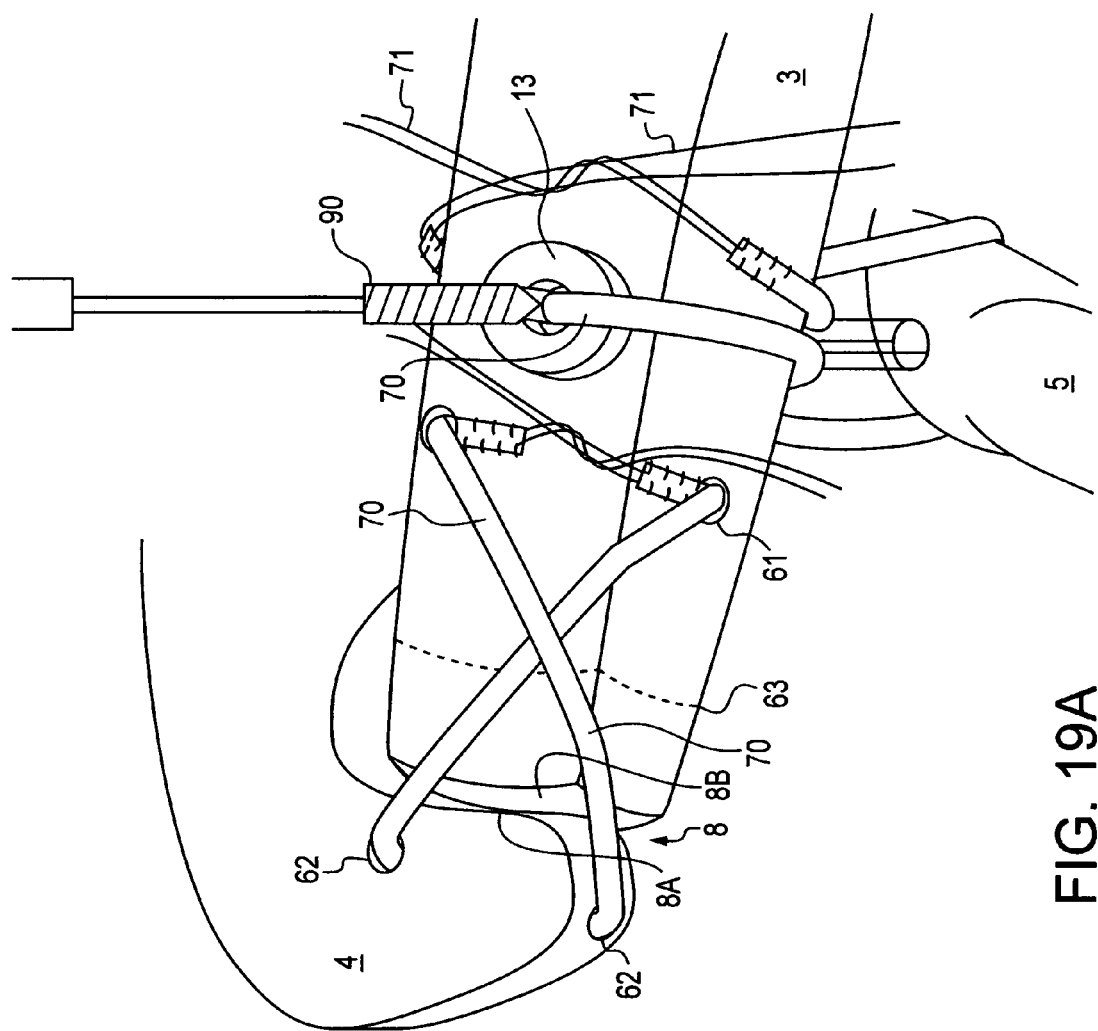
FIG. 19A is a schematic view of an interference screw device being inserted into the second bone attachment component of the joint repair tool to secure the soft-tissue graft used to reconstruct the coracoclavicular ligaments
Figure 19B:
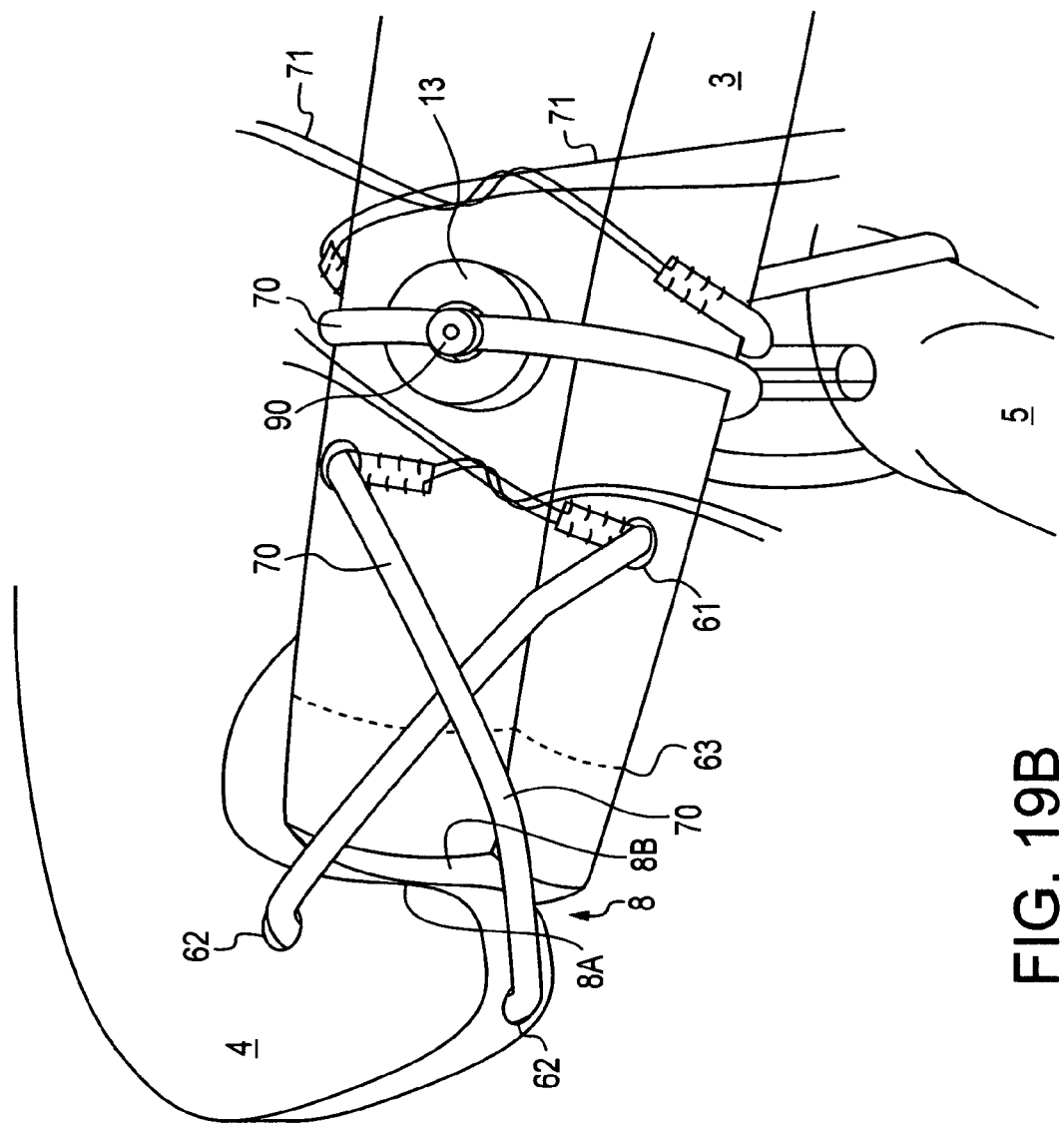
FIG. 19B is a schematic view of an interference screw device inserted into the second bone attachment component of the joint repair tool to secure the soft-tissue graft used to reconstruct the coracoclavicular ligaments

To reconstruct the coracoacromial (CC) ligaments, free graft 70 with sutures 71 may be passed around the base of the coracoid process 5 of scapula 2 and clavicle 3 and through second bone component 13 of the joint repair tool 10, as in FIGS. 17 and 18. With free graft 70 in position at the CC joint, the ends with attached sutures 71 are tensioned and secured by tying or fastening the sutures. Additionally, a conventional interference fixation device or screw may be inserted into the second bone attachment component 13 adjacent the soft-tissue graft to assist in securing the CC ligament reconstruction (See FIGS. 19A and 19B).

Figure 20:
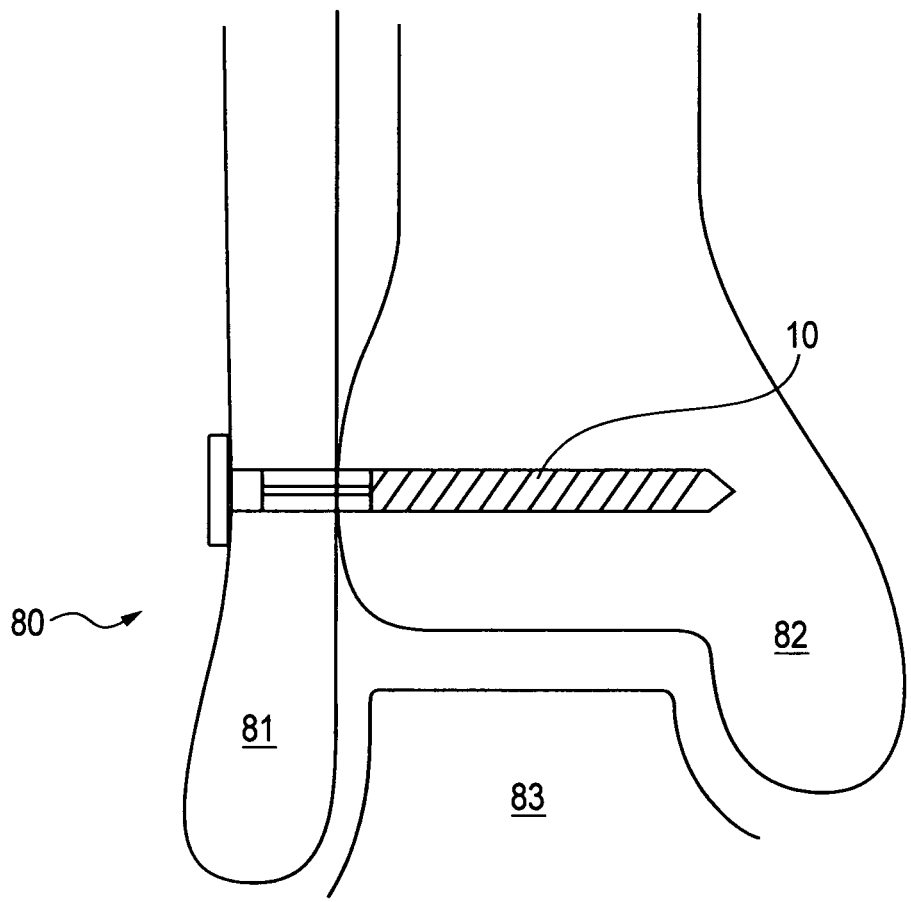
FIG. 20 is a perspective view of the joint repair tool of FIG. 3 applied to the fibula and tibia of an ankle joint to restore the proper relationship between adjacent bearing articular joint surfaces of the fibula, tibia and talus of the ankle joint in accordance with the present invention.

The joint repair tool 10, with its associated methods and devices described above, can be utilized in different anatomic locations to perform joint repair and reconstruction by restoring the proper relationship between adjacent bearing articular surfaces such as 8A and 8B. For example, tool 10 may be used in repairing and reconstructing an ankle syndesmosis 80 as shown in FIG. 20 by placing tool 10 across fibula 81 and into tibia 82. The design and size of tool 10 and its associated devices will, of course, vary according to the size and dimensions of the injured joint and its bones.

From all of the foregoing it will be evident that, although particular forms have been illustrated and described, nevertheless various modifications can be made without departing from the true spirit and scope of the invention. Accordingly, no limitations are intended by the foregoing description and the accompanying drawings, and the true spirit and scope of the invention are intended to be covered by the following claims.

I claim:

1. An instrument for repairing separated bones of a joint comprising
    a first component which includes means for being affixed to a first bone of a separated joint at a location spaced apart from surfaces in the joint bearing against each other,
    a second component which includes means for being affixed to a second bone of the separated joint at a location spaced apart from surfaces in the joint bearing against each other, and
    a mobile component having a length which is adjustable to a predetermined distance joined to and flexibly connecting the first and second components limiting independent movement between the first and second components and bones and allowing normal physiological motion of the bones and their joint surfaces.

2. An acromioclavicular joint injured by a separation of the clavicle and scapula comprising
    a first component of an instrument for repairing the joint affixed in the scapula,
    a second component of the instrument for repairing the joint having a length affixed in the clavicle, and
    a mobile component of the instrument for repairing the joint having a length which is adjustable to a predetermined distance joined to and flexibly connecting the first component in the scapula to the second component affixed in the clavicle having a limited range of movement to restrict independent movement between the clavicle and the scapula and to allow normal physiological motion of the clavicle and scapula and their joint surfaces.

3. The instrument of claim 1 in which the first component and the second component are aligned for an aligned installation in the first and second bones.

4. The instrument of claim 1 in which the second component includes a stop member arranged to contact an outer surface of the second bone and limit the distance to which the second component extends into the second bone.

5. The instrument of claim 1 in which the means for the first component to be affixed in the first bone includes a threaded section.

6. The instrument of claim 1 in which the means for the components to be affixed in the bones is an adhesive.

7. The instrument of claim 1 in which the mobile component is at least one flexible wire.

8. The instrument of claim 1 in which the mobile component is at least one suture.

9. The instrument of claim 1 in which the first component and the second component each include a centrally disposed socket alignable with each other and having irregular inner surfaces for engagement by a driving tool.

10. The instrument of claim 9 in which the sockets in the first and second components are arranged in alignment with each other for simultaneous engagement by the driving tool.

11. The instrument of claim 9 in which the sockets in the first and second components are arranged in alignment with each other for simultaneous engagement by a single driving tool.

* * * * *